(12) United States Patent
Kamlag et al.

(10) Patent No.: US 8,840,930 B2
(45) Date of Patent: Sep. 23, 2014

(54) PHARMACEUTICAL COMPOSITION FOR INHALATION

(75) Inventors: Yorick Kamlag, Paehl (DE); Morgane Lejeune, Munich (DE); David Alexander Vodden Morton, Williamstown (AU)

(73) Assignee: Sanofi SA, Meyrin (CH)

( * ) Notice: Subject to any disclaimer, the term of this patent is extended or adjusted under 35 U.S.C. 154(b) by 0 days.

(21) Appl. No.: 13/202,081

(22) PCT Filed: Feb. 18, 2010

(86) PCT No.: PCT/EP2010/052026
§ 371 (c)(1),
(2), (4) Date: Dec. 1, 2011

(87) PCT Pub. No.: WO2010/094731
PCT Pub. Date: Aug. 26, 2010

(65) Prior Publication Data
US 2012/0071449 A1     Mar. 22, 2012

(30) Foreign Application Priority Data
Feb. 18, 2009 (EP) .................................... 09153082

(51) Int. Cl.
| A61K 9/14  | (2006.01) |
| A61K 9/72  | (2006.01) |
| A61K 45/06 | (2006.01) |
| A61K 9/00  | (2006.01) |

(52) U.S. Cl.
CPC ............... *A61K 9/0075* (2013.01); *A61K 45/06* (2013.01)
USPC ......................................... 424/493; 428/402

(58) Field of Classification Search
CPC ...... A61K 9/0075; A61K 9/1623; A61K 9/14
See application file for complete search history.

(56) References Cited

U.S. PATENT DOCUMENTS

| 5,478,578 A | 12/1995 | Arnold et al. |
| 7,521,438 B1 | 4/2009 | Szelenyi et al. |
| 2004/0152720 A1 | 8/2004 | Hartig et al. |
| 2004/0241232 A1 * | 12/2004 | Brown et al. ................ 424/469 |
| 2005/0118113 A1 * | 6/2005 | Caponetti et al. ............ 424/46 |
| 2005/0175549 A1 | 8/2005 | Goede et al. |

FOREIGN PATENT DOCUMENTS

| DE | 199 47 235 A1 | 4/2001 |
| GB | 2 395 900 A | 6/2004 |
| WO | WO 01/89492 A | 11/2001 |
| WO | WO 2006/099591 A1 | 9/2006 |
| WO | WO 2009/010770 A | 1/2009 |

OTHER PUBLICATIONS

US Pharmacopeia (Metered-Dose Inhalers and Dry Powder Inhalers, Chp. 601, pp. 1-32, accessed at http://www.pharmacopeia.cn/v29240/usp29nf24s0__c601s17.html, May 1, 2013.*
Hulse et al. (Drug Development and Industrial Pharmacy, 35(6): 712-718 (2009).*
de Boer et al., International Journal of Pharmaceutics, 260: 201-216 (2003).*
Ogorodova, L., et al., "Means for inhalational delivery of drugs: doctor's view and patient's view," pp. 33-36 (2002).
Tsoy, A., "Dry powder inhalations—the most effective way of delivering drugs in the treatment of chronic obstructive pulmonary diseases," 5 pgs (2008).
European Medicines Agency Inspections, Committee for Medicinal Products for Human Use (CHMP), "Guideline on Excipients in the Dossier for Application for Marketing Authorisation of a Medicinal Product," 12 pgs. (London, Nov. 6, 2006).

* cited by examiner

*Primary Examiner* — Kortney L Klinkel
*Assistant Examiner* — Lisbeth C Robinson
(74) *Attorney, Agent, or Firm* — Kilpatrick Townsend & Stockton LLP

(57) ABSTRACT

The present invention relates to a pharmaceutical composition for inhalation. The invention is further directed to a method for setting the performance characteristics of such a pharmaceutical composition and the use of such a composition in the treatment of asthma, COPD, allergies, infectious diseases and diseases of the cardiovascular system.

10 Claims, 7 Drawing Sheets

Principal blending process

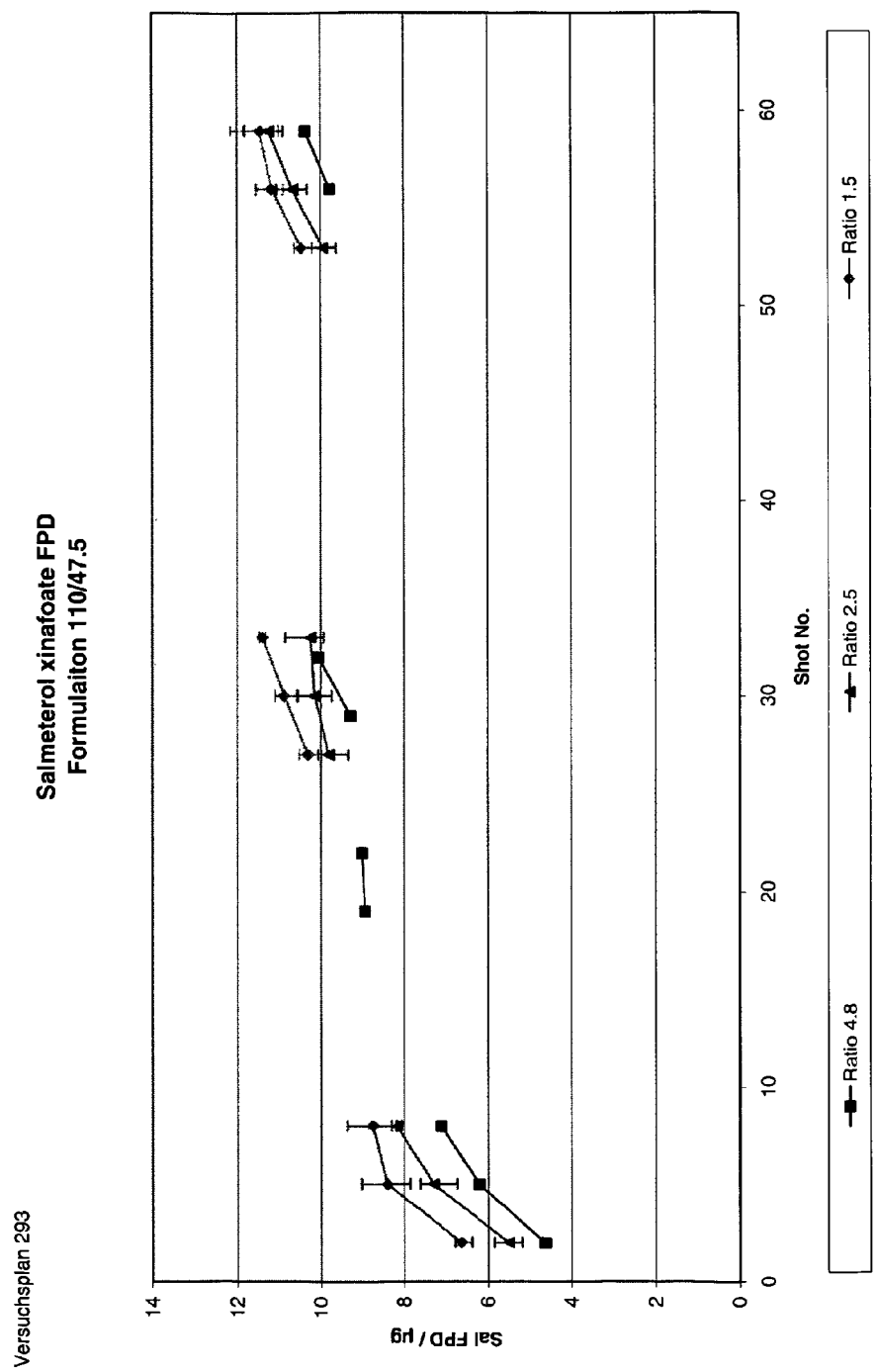
Figure 2: Salmeterol xinafoate fine particle dose – low dose strength

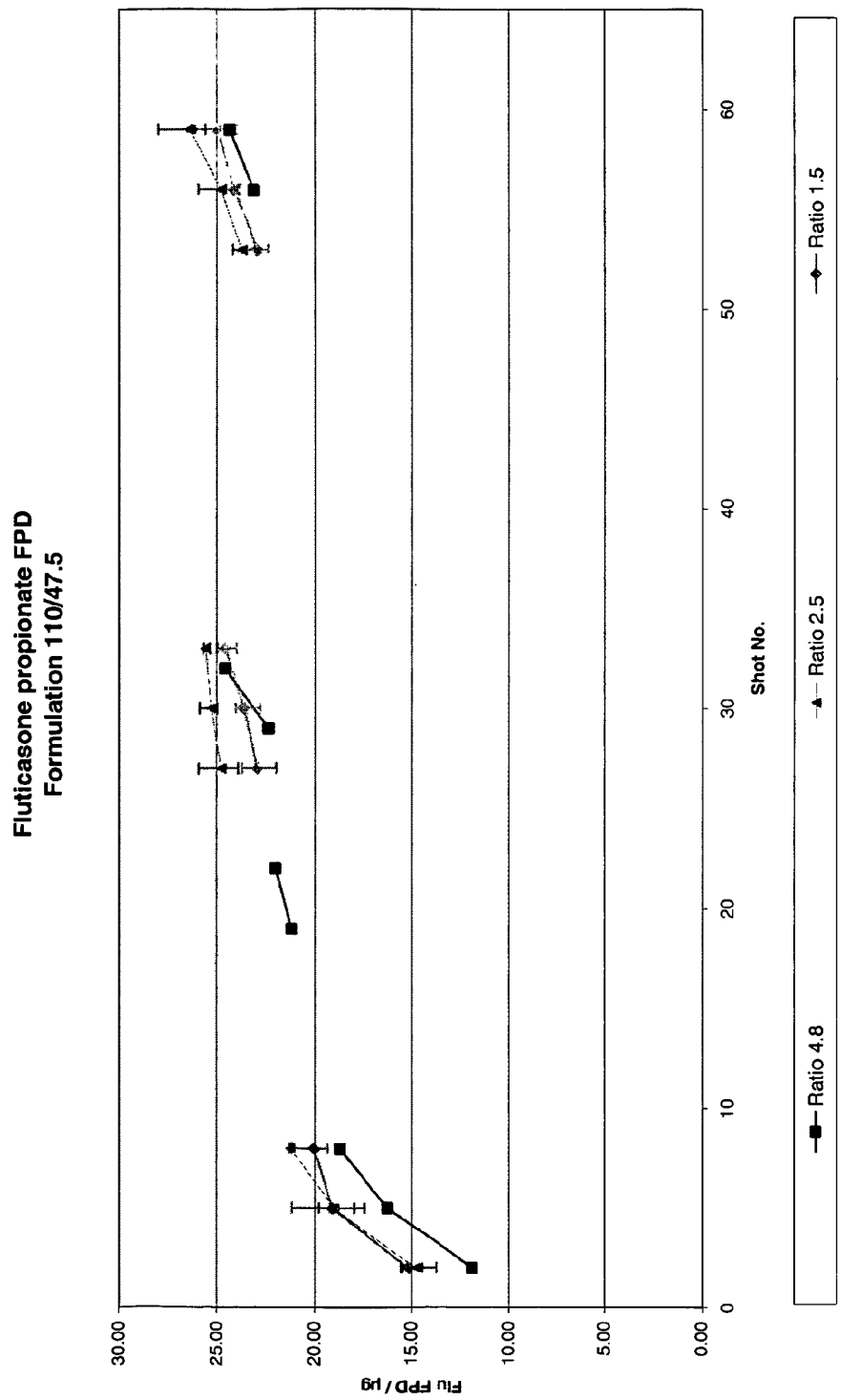
Figure 3: Fluticasone propionate fine particle dose – low dose strength

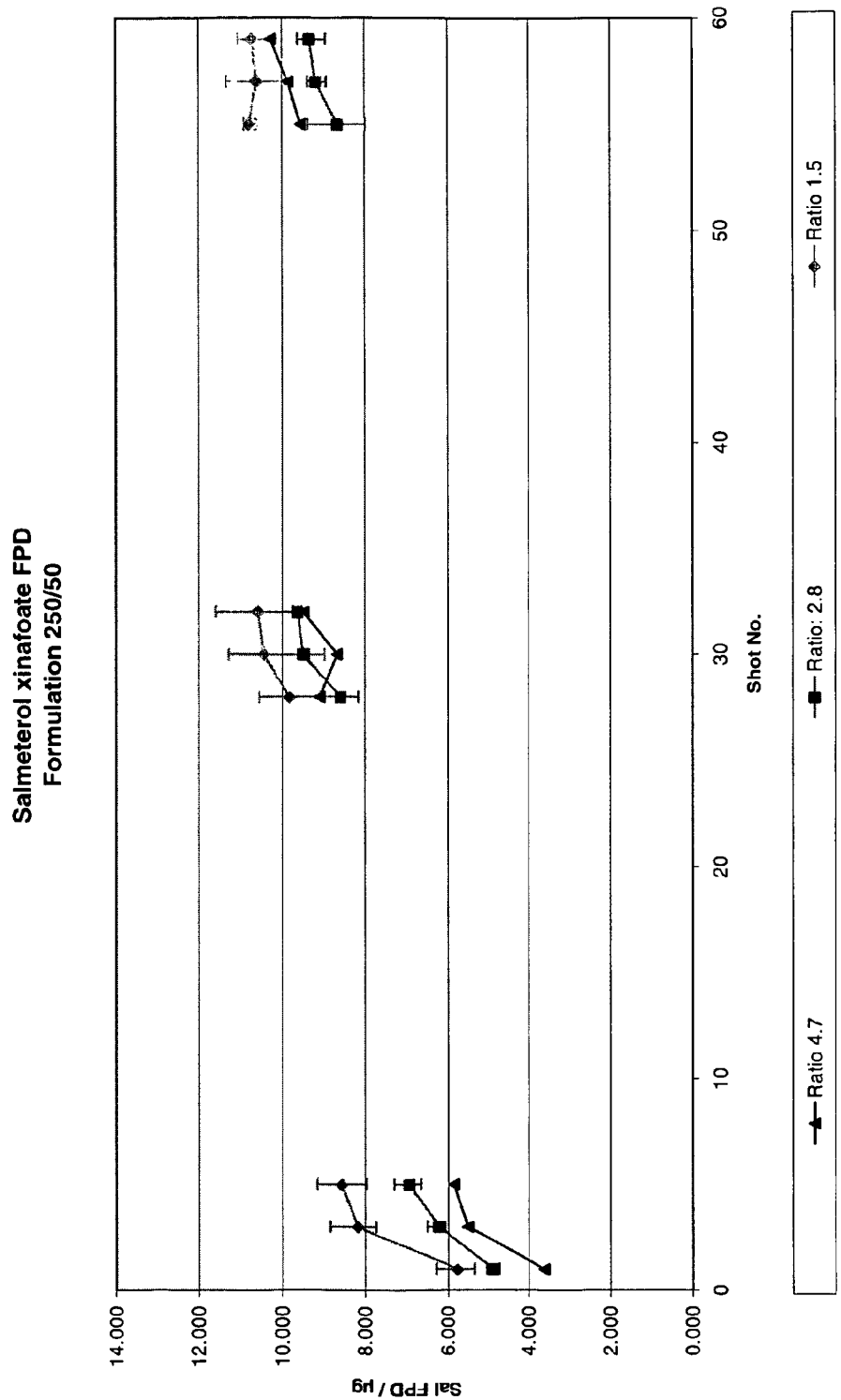
Figure 4: Salmeterol xinafoate fine particle dose – Middle dose strength

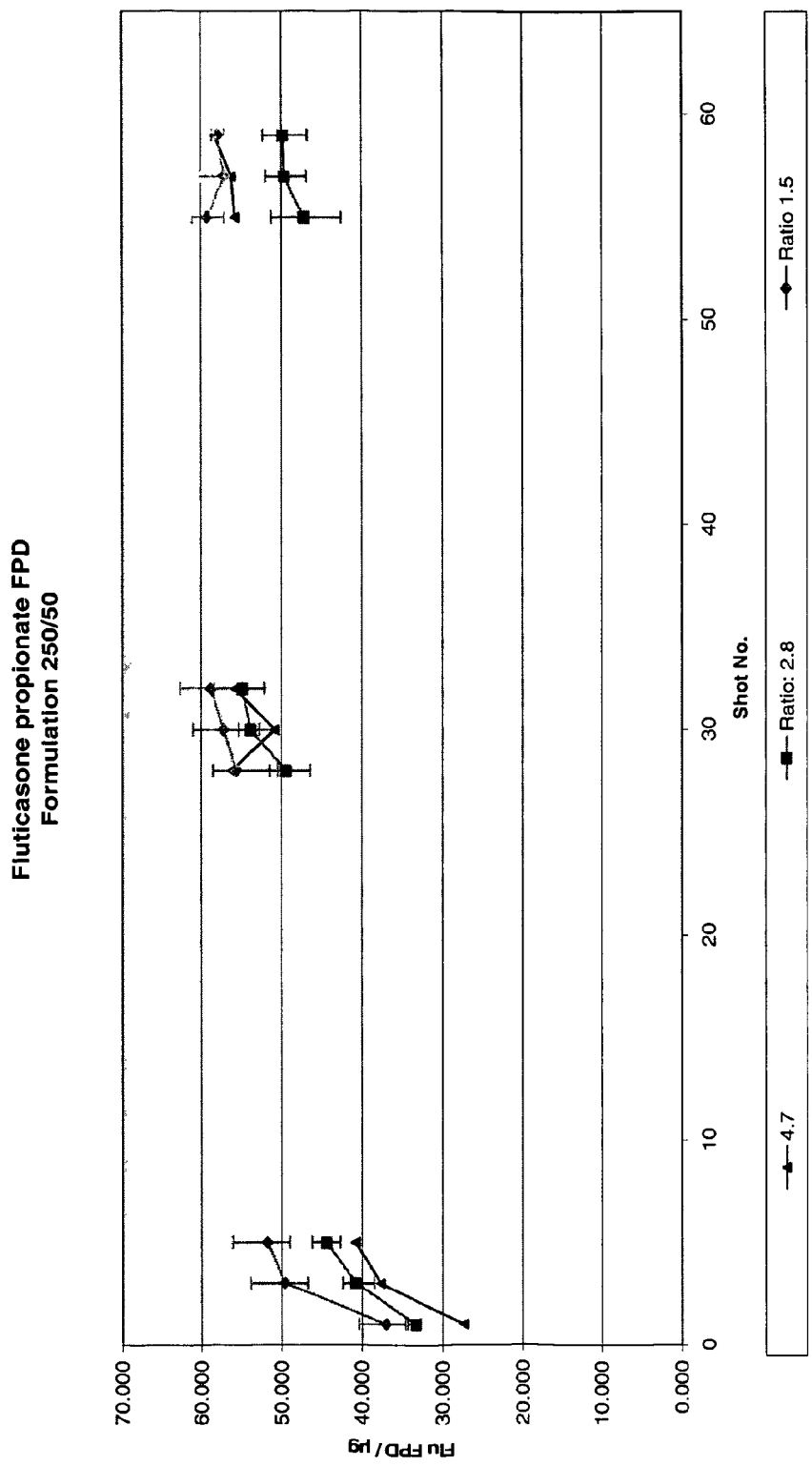
Figure 5: Fluticasone propionate fine particle dose – Middle dose strength

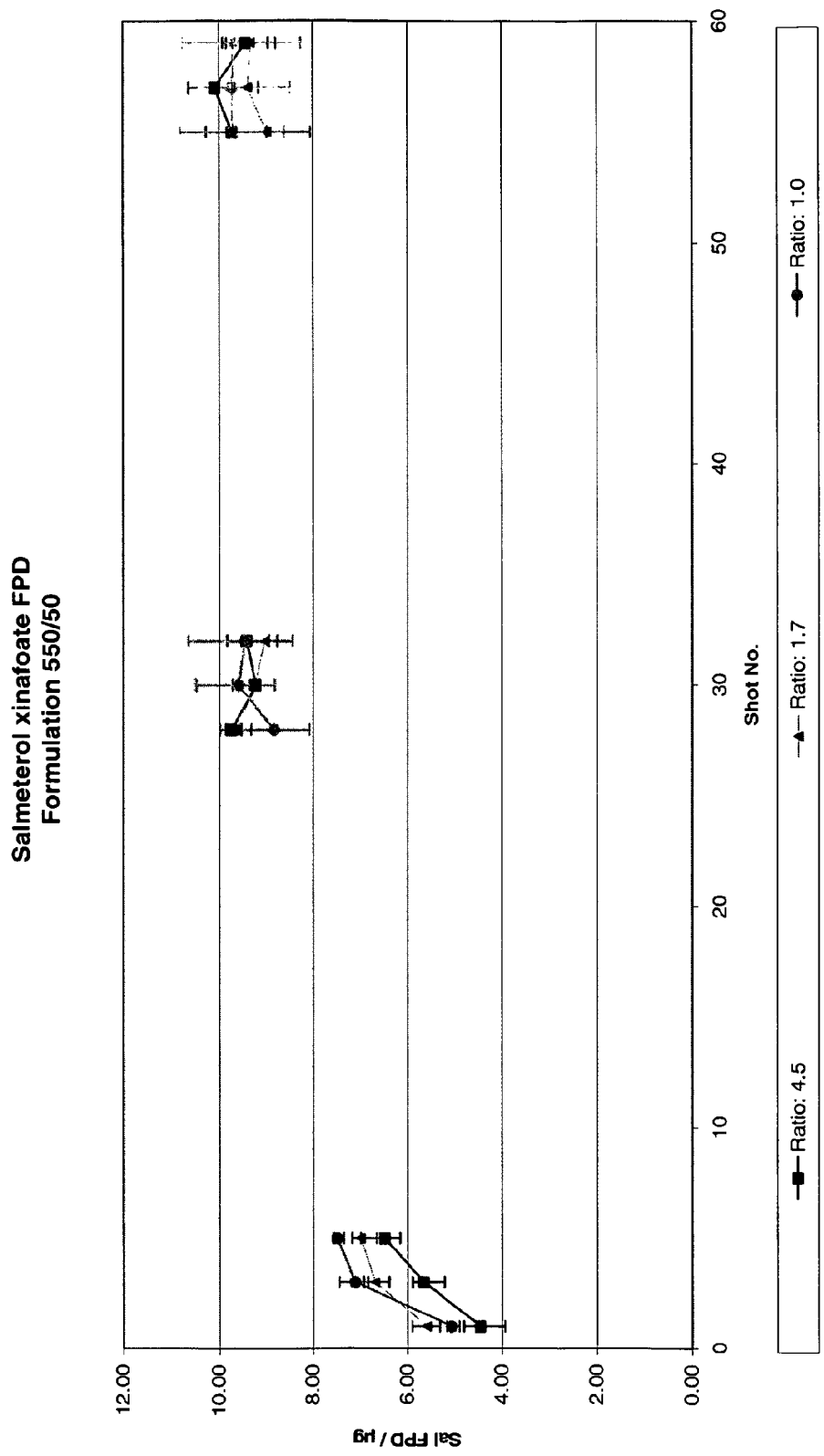
Figure 6: Salmeterol xinafoate fine particle dose – high dose strength

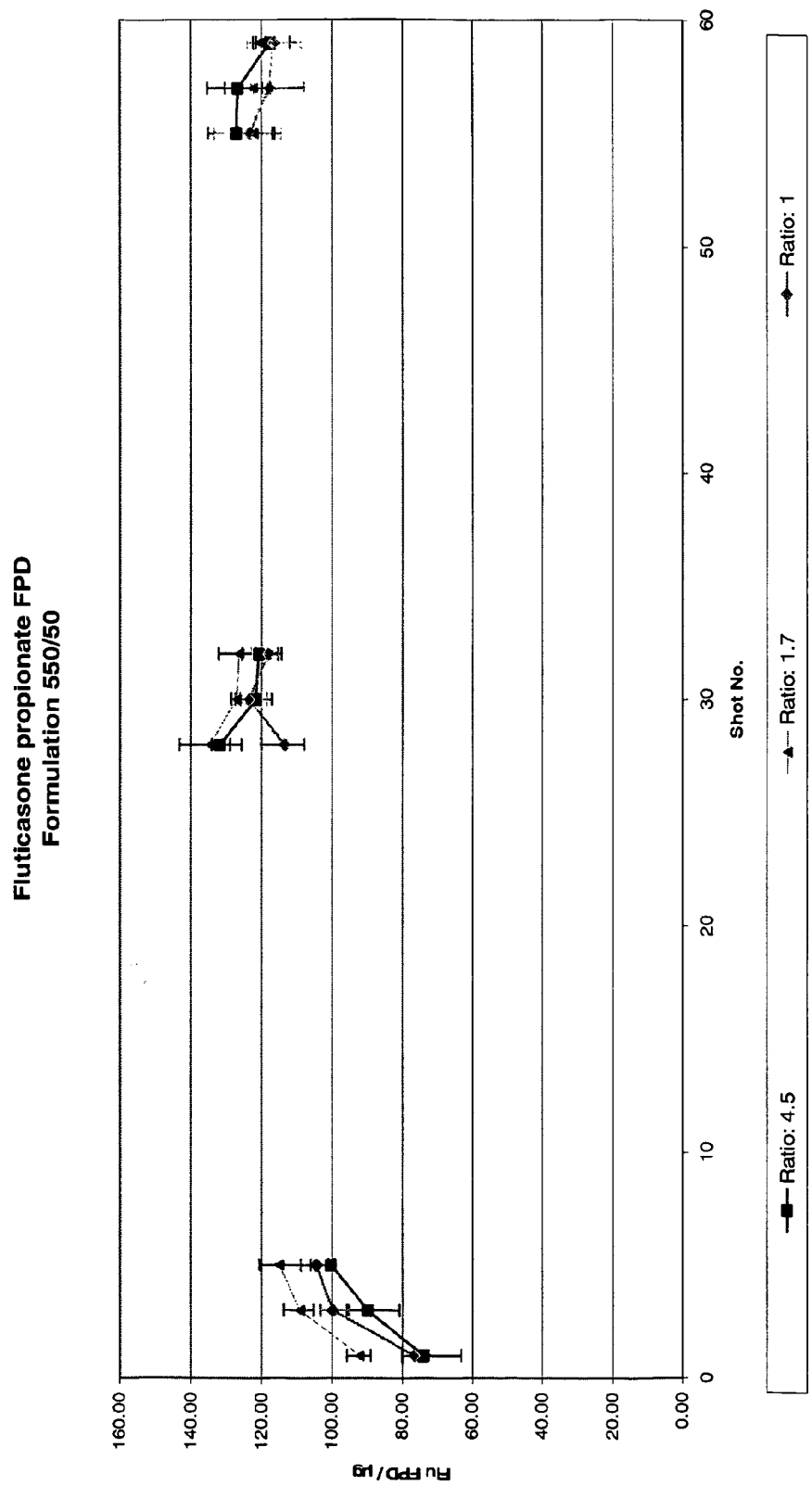
Figure 7: Salmeterol xinafoate fine particle dose – high dose strength

PHARMACEUTICAL COMPOSITION FOR INHALATION

CROSS-REFERENCE TO RELATED APPLICATIONS

This application is a U.S. National Stage Application of PCT/EP2010/052026, filed Feb. 18, 2010, which claims the benefit of European Application No. 09153082.4, filed Feb. 18, 2009, the entire contents of which are incorporated by reference herein.

FIELD OF THE INVENTION

The present invention relates to a pharmaceutical composition for inhalation. The invention is further directed to a method for setting the performance characteristics of such a pharmaceutical composition and the use of such a composition in the treatment of asthma, COPD, allergies, infectious diseases and diseases of the cardiovascular system.

BACKGROUND OF THE INVENTION

In inhalation therapy, a pharmaceutical delivery device, such as a dry powder inhaler ("DPI"), is typically employed to deliver a prescribed dose of a pharmaceutical composition and, hence, medicament to the pulmonary system of a patient. The active compound must be inhalable. In order to be able to pass into the lungs, it must be present in particles of size about 0.5 to 10 μm. Such particles can be obtained, for example, by micronization, controlled precipitation from suitable solvents or by spray drying if the process conditions are suitably selected, controlled and carried out. In a typical DPI, a dose of the pharmaceutical composition is positioned in an aerosolization chamber, where it is aerosolized and, hence, dispersed into respirable particles by airflow supplied by the patient's inspiration effort. It is also well known in the art that in order to settle in the appropriate regions of the lung associated with local and/or systemic drug delivery, the dispersed particles must be of suitable size.

The pulmonary system includes the upper airways, including the oropharynx and larynx, followed by the lower airways, which include the trachea followed by bifurcations into bronchi and bronchioli. The upper and lower airways are called the conducting airways. The terminal bronchioli then divide into respiratory bronchioli, which then lead to the alveolar region, or the deep lung.

It is well known that medicament particles deposit in specific areas of the pulmonary system based upon the aerodynamic size of the particles and the flow rate of the air within which they are entrained. Typically, with average inhalation flow rates of between 30 and 90 liters per minute, particles having an aerodynamic diameter in the range of 0.5 to 3 μm are suitable for systemic delivery, as these particles deposit selectively in the deep lung. As mentioned above, particles having an aerodynamic diameter in the range of approximately 0.5 to 10 μm are suitable for local lung delivery.

Particles having an aerodynamic diameter greater than 10 um generally deposit in the mouth, throat or upper airways, offering little therapeutic benefit. Particles having an aerodynamic diameter less than 0.5 μm do not settle out of the air flow to deposit in the lungs, and are subsequently respired when the patient exhales.

The size or diameter of the particles, thus, is crucial for the therapeutic effect of a pharmaceutical composition for inhalation. Efforts in this area have included the use of excipients, such as milled or micronized lactose, to dilute the medicament in the pharmaceutical composition, allowing microgram quantities of very potent medicaments to be precisely metered into milligram sized doses with an acceptable degree of control. By controlling the size ranges of the excipient powders, gains have been reported in flowability, dispersability and aerosolization of dry powder medicament formulations.

In an effort to increase the aerodynamic properties (aerosolizibility and dispersability) of the particles delivered to the selected target region of the lungs, recent efforts have led to a departure from the use of medicament particles milled to respirable size and then blended with excipient carriers.

For example, according to WO 99/16419, prior art compositions containing milled respirable drug particles and large excipient carrier particle systems may allow for at least some medicament particles to loosely bind to the surface of the large carrier surface and disengage upon inhalation, but a substantial amount of the medicament fails to disengage from the large lactose particles and is deposited in the throat. To allow undesirable throat deposition to be reduced, WO 99/16419 discloses microporous microparticles containing a medicament, an excipient (i.e. lactose) and surfactant.

WO03/024396 discloses a pharmaceutical composition comprising a medicament fraction of medicament particles having a mass median aerodynamic diameter no greater than approximately 10 μm; and at least 50% of a non-respirable excipient fraction, said non-respirable excipient fraction comprising low density excipient particles having an aerodynamic diameter greater than approximately 10 μm and a geometric diameter greater than approximately 30 μm.

US 2005/175549 discloses an inhalable dry powder mixture comprising effective amounts of two API's, optionally together with a pharmaceutically acceptable carrier. The carrier might be finely divided and may be selected from sugars such as lactose. However, there is no indication to use different particle sizes for the respective carrier and there is no indication that the relation of the carriers in the composition may be used to set specific characteristics of the inhalable mixture.

In pharmaceutical compositions for inhalation with two or more active substances, the tuning of the aerodynamic diameters is problematic. The aerodynamic diameter of a formulation is a parameter, which determines how deep the particles will intrude into the respiratory tract: the smaller it is the deeper the particles will enter. The tuning of the aerodynamic diameter of the inhaled formulation is needed to ensure the intrusion of the active ingredient into the desired part of the respiratory tract to unfold its full potential.

Especially with two or more active substances, which possibly should have different desired depth of intrusion into the respiratory tract, the tuning is very difficult, because of interactions between excipients with active substances and active substances with each other. With common preparation techniques for inhalation compositions the tuning can not be adjusted properly, because the arrangement of the adherence of active ingredients at the excipient carrier is quite randomly.

Since there is a growing demand for inhalation compositions for use in combination therapy involving two or more active agents, the development of new formulations providing a tailored administration of different inhalable drugs at one time to a patient in a precise and uniform amount is highly needed.

SUMMARY OF THE INVENTION

Therefore, it is an object underlying the present invention to provide a pharmaceutical composition for inhalation containing more than one active ingredient, wherein the interactions between the different active ingredients are considerably reduced. It is a further object of the present invention to provide a pharmaceutical composition of the above kind for inhalation having better stability, homogeneity and providing higher bioavailability of the active ingredients involved. It is a still further object of the invention to present a formulation of a pharmaceutical composition, allowing to lower the amount of active agent per single dose for a given therapy compared with state-of-the-art compositions. A still further object is to provide a pharmaceutical composition allowing a tailored administration of the different active ingredients contained therein and to deliver them to the intended area of action in the respiratory system of a patient and in a predetermined amount. It is a further object of the invention to make a method of manufacturing for those pharmaceutical compositions and a method for setting the performance characteristics of those pharmaceutical compositions available.

These objects are solved by the subject-matter of the independent claims. Preferred embodiments are indicated in the dependent claims.

The present invention is based on a new approach of manufacturing pharmaceutical compositions and of setting the performance characteristics of them and their use for inhalation therapy. Each different active ingredient will be blended in a preblending procedure with a suitable excipient. This procedure may include different mixing steps to ensure a proper adherence of the active ingredient at the excipient carrier. The preblending procedure may differ from one active substance to the other. The obtained preblends are then blended together in the main blending procedure, which contains different mixing steps with less intensity to obtain a homogenous mixture without breaking the adherence from the preblending steps.

By using this approach, the following unexpected effects could be achieved:

The aerodynamic diameter for particles with one active substance can be tuned independently from particles with another active substance. Therefore the entry of each active substance into the respiratory tract can be adjusted properly. Further, the active substances have less interactions with each other in the final composition, the stability of the composition is enhanced, the homogeneity of the composition is easier to obtain, the effect of the active substance is enhanced and a smaller amount of active ingredient is needed for the same effect compared with common compositions.

Therefore, the present invention makes a new formulation for inhalation in combination therapy available and a method for setting the performance characteristics of it.

DESCRIPTION OF THE FIGURES

FIG. 2-7 show the fine particle dose (FPD) of the formulations according to table 2.

DETAILED DESCRIPTION OF THE INVENTION

Figure 1:
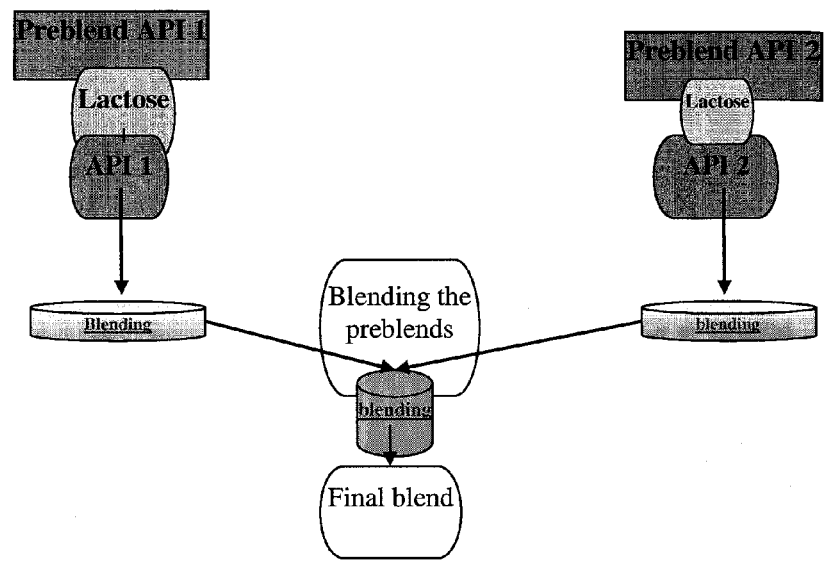
FIG. 1 shows details of the principal blending process according to the present invention.

In a first aspect, the present invention provides a method for setting the performance characteristics of a pharmaceutical composition for inhalation, comprising the steps of:
a) providing at least two preblends each containing a mixture of an active pharmaceutical ingredient and a suitable excipient;
b) mixing the at least two preblends; and
c) introducing the mixture in a suitable delivery device capable of delivering the medicament fraction to the pulmonary system of a patient, characterized in that the weight ratio of the excipients of the at least two preblends is set between 1-5.

Surprisingly, it turned out that the characteristics of a pharmaceutical composition for inhalation, such as the fine particle fraction (FPF) or fine particle dose (FPD) of the respective API, may be influenced by setting the weight ratio of the excipients used in the different preblends to a specific value. Herein, it is contemplated that a weight ratio between the excipients used in the different preblends of between 1-5 (including the values of 1 and 5) is suitable to fine tune the FPF or fine particle dose (FPD) of the active ingredients.

If more than two preblends are used, the ratio of 1-5 reflects the weight ratio of the largest excipient weight in one preblend to the smallest excipient weight in another preblend.

The performance characteristics of the composition may be further influenced by using high shear and/or low shear mixing in step a) and/or b). As it can be seen in example 3, this might involve also settings, wherein both types of mixing are used.

According to a preferred embodiment, the excipient used in the different preblends is the same or different. If they are different, the excipients may be chemically different and/or may differ in their particle size. In the latter case, it is a preferred embodiment that the d50 value of the individual excipients differs by more than 10%, preferably more than 15%, most preferably more than 20%.

Thus, according to an aspect, the present invention provides a pharmaceutical composition for inhalation, containing a medicament fraction of at least two active pharmaceutical ingredients and at least two pharmaceutically acceptable excipients, wherein the active pharmaceutical ingredients are adhered to said excipients, and wherein each active ingredient is adhered to a different excipient, characterized in that the d50 value of the individual excipients differs by more than 10%, preferably more than 15%, most preferably more than 20%.

The d50 value is also known as Median diameter or Medium value of particle diameter, and it is the particle diameter value in case cumulative distribution percentage reaches 50%. It is one of the important parameters representing characteristics of particles. For example, if d50 is 5 μm, then there are 50% particles larger than 5 μm, 50% smaller than 5 μm.

The present invention contains at least two different kinds of active pharmaceutical agents, adhered independently to at least two excipients. That is to say, the invention encompasses also cases, wherein three or more active agents are combined in one pharmaceutical application. But in standard cases, the usual number of active agents will be two, or a maximum of three active agents.

The term "adhered" as used herein means any kind of reversible bonding between the individual particles of the active agents and the excipients. This includes adherence by ionic bonding, covalent bonding, or also weaker bonds such as hydrogen bridges and van der Waals forces.

The term "different" as used above means that the particle size (d50 value) of the excipients differs in the way described above. It does not necessarily mean that the excipients must be chemically different although this is not excluded by this definition.

As outlined above, it is a preferred embodiment of the present invention that the d50 value of the individual excipients differs by more than 10%. It surprisingly turned out that the positive effects of the present invention, in particular less interactions of the individual active ingredients with each other in the final composition, enhancement of the stability of the composition, better homogeneity of the composition, and, importantly, that the effect of the active substance is enhanced and a smaller amount of active ingredient is needed for the same effect compared with common compositions, may be reached if the d50 value of the individual excipients differs by more than 10%.

As it can be seen in Table 1 and from the results contained therein, by providing (and mixing) preblends with excipients which d50 differs by more than 10%, the fine particle fraction (subsequently also designated by FPF) of each API may be influenced, in this precise case, decreased.

The active ingredient present in the compositions of the present invention can fundamentally be any desired pharmaceutically active compound which can be administered by inhalation in dry powders. In order that the active compound is inhalable, i.e. can pass into the lung, it must be present in particles having a mean particle diameter of at most approximately 10 µm, for example approximately 1 to 10 μm and preferably approximately 1 to 6 μm. Such particles can be obtained in a manner which is known per se, for example by micronization, controlled precipitation from suitable solvents (e.g. even from supercritical carbon dioxide) or by spray drying if the process conditions are suitably selected, controlled and carried out. The term "fine particle" as used herein denotes particles having a mean particle size of 5 μm and below.

According to a preferred embodiment, the at least two active ingredients are independently selected from the group consisting of active ingredients suitable for inhalation, preferably analgesic, antiallergenic, antibiotic, antiinfective, antihistamine, anti-inflammatory, antitussive agents, bronchodilators, anticholinergic drugs, hormones, xanthines, vaccines, therapeutic proteins, peptides, and combinations thereof, more preferably albuterol, beclometasone, budesonide, carmoterol, ciclesonide, fenoterol, fluticasone, formoterol, indacaterol, ipratropium, mometasone, salbutamol, salmeterol, tiotropium and pharmaceutically acceptable salts or solvates thereof.

In the case of compositions which contain at least one pharmaceutically active ingredient in the form of a pharmaceutically acceptable salt, this salt may be selected from a chloride, bromide, iodide, nitrate, carbonate, sulfate, methylsulfate, phosphate, acetate, benzoate, benzenesulfonate, fumarate, malonate, tartrate, succinate, citrate, lactate, gluconate, glutamate, edetate, mesylate, pamoate, pantothenate or hydroxy-naphthoate salt. It may also be present as a pharmaceutically acceptable ester, for example an acetate, propionate, phosphate, succinate or etabonate.

The amount of active compound in the formulations obtainable according to the invention can vary within wide ranges and is to a high extent dependent on the respective active compound and up to a certain degree also on the powder inhaler used. Typically, the active compound concentration can be approximately 0.1 to 10% by weight, in particular approximately 0.1 to 5% by weight, based on the total formulation. Occasionally, higher or lower concentrations can also be expedient, where, however, active compound concentrations of below 0.001% by weight or below 0.01% by weight rarely occur.

Basically all excipient (or carrier) materials customarily used in dry powder formulations are suitable, for example mono- or disaccharides, such as glucose, lactose, lactose monohydrate, sucrose or trehalose, sugar alcohols, such as mannitol or xylitol, polylactic acid or cyclodextrin, glucose, trehalose and in particular lactose monohydrate are suitable.

Preferred, however, are the excipients selected from the group consisting of sugars and saccharides, preferably inhalation grade lactose, more preferably alpha monohydrate lactose in the form of crystalline lactose, milled lactose or micronized lactose.

The excipient is preferably present in the composition of the invention in a particle size which is not inhalable. The carrier particles, however, should on the other hand not be too large, as this can have a disadvantageous effect on the FPF. Thus, in a preferred embodiment, the medicament fraction of the composition comprises two excipients having a d50 value of about 125-145 μm and about 50-100 μm, respectively.

If desired, in addition to noninhalable excipient particles, the formulation can also contain a proportion of inhalable excipient particles; for example in addition to relatively coarse lactose monohydrate carrier particles it can contain a proportion of, for example, 0.1 to 10% by weight of micronized lactose monohydrate, which can have, for example, a particle size diameter of at most 10 μm, preferably at most 5 μm, for at least 50% of the particles.

Among the most preferred excipients is commercially available alpha lactose monohydrate of pharmaceutical grade. Those with a d50 value of about 185-215 (coarse lactose), those with a d50 value of about 125-145 μm (fine lactose) and those with a d50 value of 50-100 μm (superfine lactose) are preferred. Therefore, a combination of these excipients (coarse, fine and superfine lactose) can advantageously be used in the present invention, since their d50 value differs by more than 10%.

The proportion of excipient material in the compositions according to the invention can vary within a wide range depending on the dilution necessary or desirable for the particular active ingredient. Usually, the proportion of the excipient material to the total medicament fraction can be, for example, approximately 80 to 99.9% by weight, where, however, higher or lower proportions can also be advantageous depending on the active ingredient.

In a further embodiment, the pharmaceutical composition is manufactured by mixing at least two preblends, each comprising one active ingredient and one excipient. This is of utmost importance to carry out the invention, since the preparation of preblends will guarantee that each individual active ingredient adheres to its specific excipient.

The dry powder formulations described can be used in all customary dry powder inhalers. They are particularly advantageous for use in multidose dry powder inhalers which contain a powder reservoir.

In a further aspect, the present invention is directed to a method for manufacturing a pharmaceutical composition for inhalation containing a medicament fraction as defined above, comprising the steps of:

a) providing at least two active ingredients and at least two pharmaceutically acceptable excipients, wherein the d50 value of the individual excipients differs by more than 10%, preferably more than 15%, most preferably more than 20%;

b) forming preblends of one active ingredient and one excipient each;

c) mixing the at least two preblends in order to provide the medicament fraction; and d) introducing the medicament fraction in a suitable delivery device capable of delivering said medicament fraction to the pulmonary system of a patient.

As outlined above, in this method, the at least two active ingredients are preferably selected from the group consisting of active ingredients suitable for inhalation, preferably analgesic, antiallergenic, antibiotic, antiinfective, antihistamine, anti-inflammatory, antitussive agents, bronchodilators, anticholinergic drugs, hormones, xanthines, vaccines, therapeutic proteins, peptides, and combinations thereof, more preferably albuterol, beclometasone, budesonide, carmoterol, ciclesonide, fenoterol, fluticasone, formoterol, indacaterol, ipratropium, mometasone, salbutamol, salmeterol, tiotropium and pharmaceutically acceptable salts or solvates thereof.

The like, the excipients are preferably selected from the group consisting of sugars and saccharides, preferably inhalation grade lactose, preferably alpha monohydrate lactose in the form of crystalline lactose, milled lactose or micronized lactose.

In a still further aspect, the present invention is directed to a pharmaceutical composition for inhalation obtainable by the method as defined above. This pharmaceutical composition preferably takes the form of an inhalant, more preferably in form of a delivery device containing the medicament fraction and one or more auxiliary agents, capable of delivering said medicament fraction to the pulmonary system of a patient.

The preferred form of such a delivery device is a dry powder inhaler (DPI). The medication in these inhalers is in the form of a dry powder that must be inhaled. There is no device or gas to propel the powder. Commercially available examples are marketed under the trademarks Rotadisk®, Diskhaler®, Diskus®, or Turbohaler®.

In a further aspect, the invention is directed to the use of a pharmaceutical composition as disclosed hereinabove for treating asthma, chronic obstructive pulmonary disease (COPD), allergies, infectious diseases and diseases of the cardiovascular system.

The present invention now will be illustrated by the enclosed Figures and the Examples. The following examples further illustrate the invention but, of course, should not be construed as limiting its scope.

EXAMPLES

Example 1

Table 1

Examples of Formulations

Formulations have been blended following the process described in FIG. 1.
Results:

TABLE 1

| | Lactose in Pre-Blend 1 | Lactose in Pre-Blend 2 | FPF API 1 | FPF API 2 |
|---|---|---|---|---|
| Formulation 1 | Lactose (D50 = 72 μm) | Lactose (D50 = 72 μm) | 47.7% | 42.7% |
| Formulation 2 | Lactose (D50 = 135 μm) | Lactose (D50 = 72 μm) | 26.3% | 36.8% |
| Formulation 3 | Lactose (D50 = 135 μm) | Lactose (D50 = 95 μm) | 20.8% | 20.3% |

It is also referred to FIG. 1, showing the blending process of the present invention for generating a formulation for use in asthma therapy.

Formulation 1 uses the same excipients in both preblends. Formulations 2 and 3 use excipients having a d50 value differing by more than 10%. The influence on the FPF of both API used is remarkable. Whereas the FPF values for Formulation 1 are 47.7 and 42.7%, respectively, they decrease dramatically in Formulations 2 and 3. Thus, the FPF is reduced improving thereby the pharmaceutical product's performance of making Formulations 2 and 3 compared to Formulation 1.

Example 2

Lactose Ratio in Pre-Blend

Results: see FIGS. 2-7

TABLE 2

The amount of lactose in each pre-blend has been modified in order to fine tune the performance profile/results of each formulation with emphasis on the first doses performance.

| Dose strength | Lactose Ratio (SalX/FluP) | Pre-Blend SalX | | Pre-Blend FluP | |
|---|---|---|---|---|---|
| | | SalX [%] | Lactose [%] | FluP [%] | Lactose [%] |
| 110/47.5 | 4.8 | 0.92 | 81.0 | 1.47 | 16.8 |
| | 2.5 | 0.92 | 70.0 | 1.47 | 27.6 |
| | 1.5 | 0.92 | 58.1 | 1.47 | 39.5 |
| 250/50 | 4.7 | 0.97 | 78.9 | 3.33 | 16.8 |
| | 2.8 | 0.97 | 70.5 | 3.33 | 25.2 |
| | 1.5 | 0.97 | 58.1 | 3.33 | 37.6 |
| 550/50 | 4.5 | 0.97 | 74.9 | 7.33 | 16.8 |
| | 1.7 | 0.97 | 58.1 | 7.33 | 33.6 |
| | 1.0 | 0.97 | 45.8 | 7.33 | 45.9 |

Conclusion:

By adjusting the lactose ratio in the pre-blends during the blending process, the FPD profile/results can be fine tuned. In example 2, by reducing the lactose ratio the FPDs increased especially at the beginning of the device life where they were much lower than for the rest of the device life. Due to this fine tuning, the overall performance of the formulation has been improved.

Example 3

Pre-Blending Process

Table 3 summarizes the FPF results of formulations done with or without pre-blend.

| Blending Process | | | | FPF API 1 | FPF API 2 |
|---|---|---|---|---|---|
| Step 1 | Step 2 | Step 3 | mixer | | |
| Pre-blend API 1 | Pre-blend API 2 | Blend preblends | Low shear Low shear High shear | 30.5% | 36.7% |
| No pre-blend | | | High shear | 42.7% | 46.4% |
| Both API pre-blended together | Extra lactose | | High shear | 44.6% | 49.2% |
| Pre-blend of API 1 only | Addition of API2 and lactose | | Low shear High shear | 47.2 | 49.0% |

Conclusion:

Pre-blending of APIs using different conditions changed the performance of the formulation. This then allows to increase or decrease the performance when necessary for the product. The use of two different blenders is also a determinating factor

The invention claimed is:

1. A method for setting the performance characteristics of a pharmaceutical composition for inhalation, comprising the steps of:

a) providing a first preblend and a second preblend each containing a mixture of an active pharmaceutical ingredient and a suitable excipient, wherein the excipient in the first preblend has a d50 value of about 125-145 μm and the excipient in the second preblend has a d50 value of about 50-100 μm, and wherein the d50 value of the excipient in the first preblend differs from the d50 value of the excipient in the second preblend by more than 20%;
b) mixing the first preblend and the second preblend; and
c) introducing the mixture in a suitable delivery device capable of delivering the medicament fraction to the pulmonary system of a patient,
wherein the weight ratio of the excipients in the first preblend and the second preblend is set between 1-5, and wherein each of the excipients in the first preblend and the second preblend is a lactose.

2. The method of claim 1, wherein the excipients in the first preblend and the second preblend are chemically the same.

3. The method of claim 1, wherein the excipients in the first preblend and the second preblend are chemically different.

4. The method of claim 1, wherein the active pharmaceutical ingredients of the first preblend and the second preblend are individually selected from the group consisting of active ingredients suitable for inhalation.

5. The method of claim 4, wherein the active pharmaceutical ingredients of the first preblend and the second preblend are individually selected from the group consisting of analgesic, anginal, antiallergenic, antibiotic, antiinfective, antihistamine, anti-inflammatory, antitussive, bronchodilator, anticholinergic drugs, hormones, xanthines, vaccines, therapeutic proteins, peptides, and combinations thereof.

6. The method of claim 5, wherein the active pharmaceutical ingredients of the first preblend and the second preblend are individually selected from the group consisting of albuterol, beclometasone, budesonide, carmoterol, ciclesonide, fenoterol, fluticasone, formoterol, indacaterol, ipratropium, mometasone, salbutamol, salmeterol, tiotropium and pharmaceutically acceptable salts or solvates thereof.

7. The method of claim 1, wherein the excipients of the first preblend and the second preblend are individually selected from the group consisting of inhalation grade lactose, milled lactose and micronized lactose.

8. The method of claim 7, wherein at least one of the excipients of the first preblend and the second preblend is alpha monohydrate lactose in the form of crystalline lactose.

9. The method of claim 1, wherein the performance characteristic set is the fine particle dose (FPD) of the active pharmaceutical ingredients of the first preblend and the second preblend.

10. The method of claim 1, wherein step a) or b) comprises high shear mixing or low shear mixing to further influence the performance characteristics.

* * * * *